(12) United States Patent
Sato et al.

(10) Patent No.: US 6,354,148 B2
(45) Date of Patent: Mar. 12, 2002

(54) REBOUND-TYPE HARDNESS TESTER

(75) Inventors: Yasunori Sato; Junichi Arai; Yuichi Minami, all of Zama (JP)

(73) Assignee: Kabushiki Kaisha Akashi (JP)

(*) Notice: Subject to any disclaimer, the term of this patent is extended or adjusted under 35 U.S.C. 154(b) by 0 days.

(21) Appl. No.: 09/777,103

(22) Filed: Feb. 5, 2001

Related U.S. Application Data

(62) Division of application No. 09/474,889, filed on Dec. 29, 1999, now abandoned, which is a division of application No. 09/032,634, filed on Feb. 27, 1998, now abandoned.

(30) Foreign Application Priority Data

Feb. 28, 1997 (JP) ............................................. 9-61787

(51) Int. Cl.$^7$ .............................. G01N 3/52; G01N 3/48
(52) U.S. Cl. .............................................. 73/79; 73/82
(58) Field of Search ........................................ 73/82, 89

(56) References Cited

U.S. PATENT DOCUMENTS

| | | | |
|---|---|---|---|
| 3,879,982 A | 4/1975 | Schmidt | 73/79 X |
| 4,270,383 A | 6/1981 | Singer et al. | 73/82 |
| 4,411,153 A | 10/1983 | Lewis | 73/79 |
| 4,885,933 A | 12/1989 | Hiestand et al. | 73/79 |
| 4,896,339 A | 1/1990 | Fukumoto | 73/81 X |
| 5,079,728 A | 1/1992 | Adams et al. | 73/82 X |
| 5,458,703 A | 10/1995 | Nakai | 148/503 |
| 5,959,198 A | 9/1999 | Pollok et al. | 73/79 |

FOREIGN PATENT DOCUMENTS

| | | | |
|---|---|---|---|
| JP | 1950 | 1/1988 | 73/79 |
| SU | 742756 | 6/1980 | 73/82 |
| WO | 34267 | 10/1996 | |

OTHER PUBLICATIONS

Abstracts of JP 10–227732A dated Aug. 25, 1998, Inventor Hayashi et al., by JPO (JP410227732A entitled "Echo Tip Type Hardness Tester") and by Derwent (Acc.–No. 1998–515995).

Abstracts of JP 10–239230A dated Sep. 11, 1998, Inventor Sato et al., by JPO (JP410239230A entitled "Echo Chip–Type Hardness Tester and Speed Detections Method of its Indentor Hammer") and by Derwent (Acc–No. 1998–545803).

*Primary Examiner*—Thomas P. Noland
(74) *Attorney, Agent, or Firm*—Adams & Wilks

(57) ABSTRACT

A rebound-type hardness tester comprises a tubular member and an indenter hammer for undergoing axial movement therein in forward and rearward directions and for impacting a specimen and rebounding therefrom. A first detecting device detects the indenter hammer during movement thereof in the forward and rearward directions. A second detecting device detects the indenter hammer after detection thereof by the first detection device during movement of the indenter hammer in the forward direction, and detects the indenter hammer before detection thereof by the first detection device during movement of the indenter hammer in the rearward direction. A measuring device measures first and second timing values corresponding to different times elapsed from the detection of the indenter hammer by the first and second detection devices. A calculating device calculates an impacting velocity and a rebounding velocity of the indenter hammer in accordance with the first and second timing values and a distance between the first and second detecting devices. A processing device calculates a hardness of the specimen in accordance with the impacting velocity and the rebounding velocity calculated by the calculating device.

12 Claims, 4 Drawing Sheets

REBOUND-TYPE HARDNESS TESTER

RELATED APPLICATION

The present application is a division of prior U.S. application Ser. No. 09/474,889 filed on Dec. 29, 1999, now abandoned, which was a division of 09/032,634 filed Feb. 27, 1998, and priority now abandoned, which are hereby incorporated by reference thereto for common subject matter is hereby claimed.

BACKGROUND OF THE INVENTION

1. Field of the Invention

The invention relates to a rebound-type hardness tester and, more specifically, to an Equotip type hardness tester in which an indenter hammer is caused to impact against a specimen and the hardness of the specimen is measured from the ratio between the velocities of the indenter hammer before and after the impaction.

2. Description of the Related Art

A rebound type hardness tester, in which an indenter hammer is caused to impact a specimen and the hardness of the specimen is calculated from the ratio between the velocity of the indenter hammer immediately before the impaction (impacting velocity) and the velocity of the same immediately after the impaction (rebounding velocity), is generally called an Equotip type hardness tester and put to practical use.

Since the indenter hammer in the Equotip type hardness tester is adapted to be shot by means of a coil spring, it is not necessarily required, in hardness measurement, that the Equotip type hardness tester is set in the position to keep the impacting direction straight down. Namely, it is possible to carry out the hardness measurement with the Equotip type-hardness tester (the body 1 formed of a cylindrical handle portion 11 and a measuring cylinder 12 connected to it) tilted, i.e., keeping the impacting direction, for example, in the horizontal direction, in an angle of depression of 45°, in an angle of elevation of 45°, and in the direction straight up (the angle of inclination then formed between the body 1 and the horizontal plane 010 is denoted by 0) and with the front end of the measuring cylinder 12 abutting on the specimen 01 as shown in FIG. 3. Thus, such an advantage is obtained that hardness of the side face of bottom face of a specimen can be freely measured.

The indenter hammer 3 is adapted to be discharged in the axial direction of the body 1 guided by the cylindrical body 1. Further, there are provided a permanent magnet within the indenter hammer 3 and a velocity detecting coil 4 wound around the front end portion of the measuring cylinder 12, and, by the movements of the permanent magnet (i.e., the indenter hammer 3), electric currents proportional to the impacting velocity and the rebounding velocity are causes to flow through the velocity detecting coil 4. The currents are converted into voltages by a voltage transformer 5 within a display unit 6, the voltages are input to a CPU 7 to calculate the hardness, and the calculated value is displayed as the Equotip hardness L of the specimen on a display 8. The Equotip hardness L is defined by a later described expression (1).

The velocity impacting the specimen 01 of the indenter hammer 3 when hardness is measured with the body 1 tilted is different from its velocity produced when the body 1 is held in the upright position. Therefore, it has so far been practiced to obtain the correct hardness value by checking the value (hardness) of the result obtained by the tilted measurement with a table (conversion table) for angular correction. There is such a one put to practical use that automatically performs the angular correction by means of an incorporated CPU. Further, there is also used a one put to practical use that automatically converts an obtained hardness value into a standardized hardness value so far in use (e.g., Brinell, Vickers, Rockwell, C, and Shore hardness) and displays the hardness value.

The principle of measurement in the Equotip type hardness tester will be described with reference to FIG. 4. Referring to FIG. 4, reference numeral 3 denotes an indenter hammer and 01 denotes a specimen. The indenter hammer 3 is shot by a coil spring (not shown) incorporated in the measuring cylinder 12 to impact the specimen and then rebound from the same.

At this time, if friction and air resistance against the indenter hammer 3 in motion is neglected and it is assumed that no external force other than the gravitational force acts on the indenter hammer 3 after it has been discharged, the hardness L of the specimen 01 is defined by the following expression $$L = (|V_2|/|V_1|) \times 1000 \tag{1}$$

where
  $V_1$: impacting velocity of the indenter hammer,
  $V_2$: rebounding velocity of the indenter hammer.

In the conventional Equotip type hardness tester, detection of the velocities of the indenter hammer 3 (the impacting velocity against and rebounding velocity from the specimen 01) is performed by measuring voltages produced in the coil at the time when the permanent magnet incorporated in the indenter hammer 3 passes by the velocity detecting coil.

Generally speaking, the voltage change occurring in the velocity detecting coil (in pulse waveform) varies with the velocity at which the permanent magnet passes by the coil. Namely, the slower the passing velocity of the permanent magnet, the duller becomes the pulse waveform W (as shown by dotted lines in FIG. 5). From this, a problem arises that accurate measurement results cannot be obtained.

Further, there is also such a problem that when the specimen is a magnetic body or it is magnetized or the environment is magnetized, an accurate result of measurement cannot be obtained due to the effect of such magnetism.

SUMMARY OF THE INVENTION

It is an object of the invention to provide a method of detecting velocities of the indenter hammer in an Equotip type hardness tester whereby the above mentioned problems are solved and an Equotip type hardness tester in which the aforesaid detecting method is carried out.

As the means for solving the above problems, a method according to the invention of detecting velocities of an indenter hammer in an Equotip type hardness tester, including a measuring cylinder constituting the body of the hardness tester and providing a passage for the indenter hammer to go forward and backward, the measuring cylinder having two light receiving holes formed therein a distance S apart in the axial direction thereof, comprises the steps of measuring the times required for the indenter hammer to go forward and backward past the two light receiving holes and detecting the velocities of the indenter hammer in accordance with the required times and the distance S.

As the means for solving the above problems, the required times are calculated by having a pulse counter, to which time pulses generated by a pulse generator are input, count the number of the timing pulses from the moment of receipt of a signal indicating that the indenter hammer passed by one light receiving hole of the two light receiving holes to the moment of receipt of a signal indicating that the same passed by the other light receiving hole.

As the means for solving the above problems, an Equotip type hardness tester according to invention comprises a measuring cylinder constituting the body of the hardness tester and providing a passage for an indenter hammer to go forward and backward, a coil spring incorporated in the body, an indenter hammer adapted to be shot by the spring force of the coil spring toward a specimen, a velocity sensor attached to the body for measuring the velocities of the indenter hammer immediately before impacting against the specimen and immediately after the impaction, and a display unit including a CPU receiving information of the velocities of the indenter hammer detected by the velocity sensor for calculating hardness of the specimen and a display for displaying thereon the hardness of the specimen calculated by the CPU, wherein the velocity sensor is constituted of two light projecting holes formed in the vicinity of the front end portion of the measuring cylinder a distance S apart from each other in the axial direction of the measuring cylinder and light receiving holes formed in the positions corresponding to the light projecting holes, and, further, light sources provided for each of the light projecting holes and photodetector devices provided for each of the light receiving holes.

In the invention, the indenter hammer, at the time of measurement, passes by the two light receiving holes formed a distance S apart in the axial direction of the measuring cylinder in the order of the inner light receiving hole and the outer light receiving hole in the impacting course, whereas it passes by them in the order of the outer light receiving hole and the inner light receiving hole in the rebounding course after impacting against a specimen.

Hence, by measuring the time required for the indenter hammer to pass by the light receiving holes in the impacting course and the time required for the same to pass by the light receiving holes in the rebounding course, the impacting velocity against and the rebounding velocity from the specimen (face) of the indenter hammer can be calculated in accordance with the measured times and the distance between the light receiving holes.

The aforesaid times can be calculated by using a pulse counter and by having numbers of timing pulses counted by the pulse counter.

Further, since the indenter hammer velocity (detecting) sensor is of a photoelectric type, it is made possible to carry out the detection having the detecting accuracy of the velocity of the indenter hammer unaffected by the indenter hammer velocity.

Further, the measurement can be carried out unaffected by magnetism.

DESCRIPTION DETAILED OF THE PREFERRED EMBODIMENTS

Figure 1:
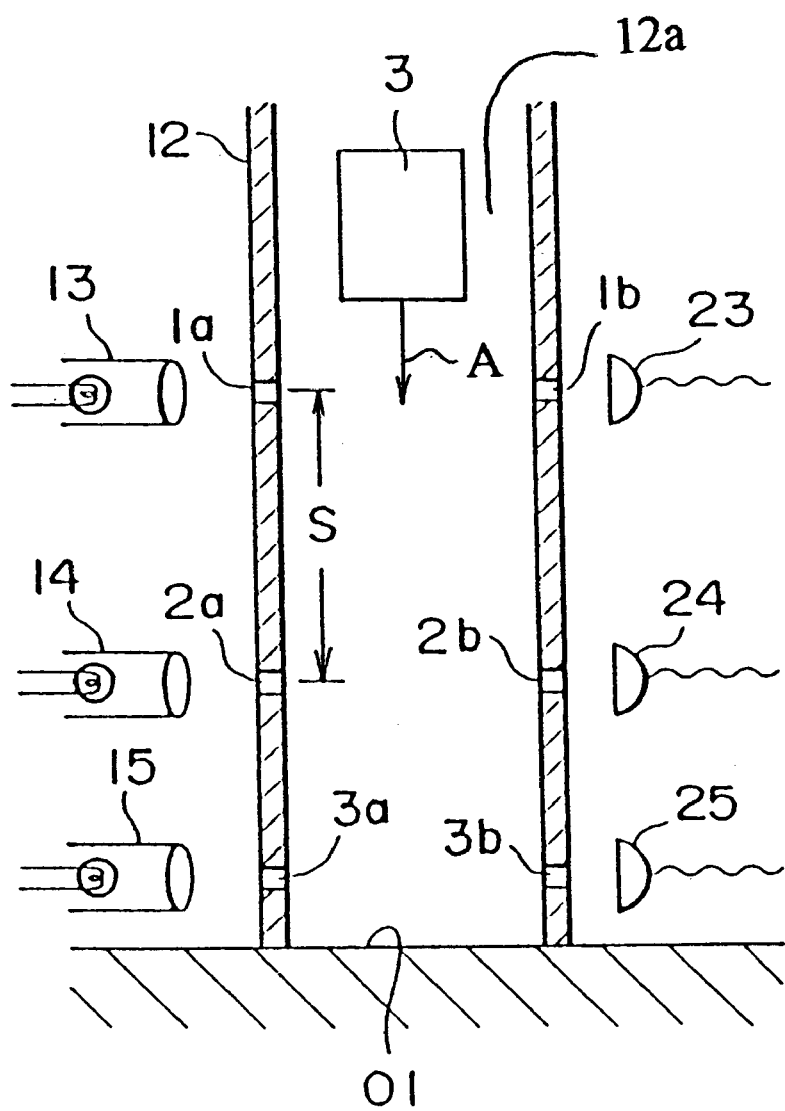
FIG. 1 is a diagram schematically showing a sensor portion for measuring the velocities of an indenter hammer in an Equotip type hardness tester as an embodiment of the invention.
Figure 2:
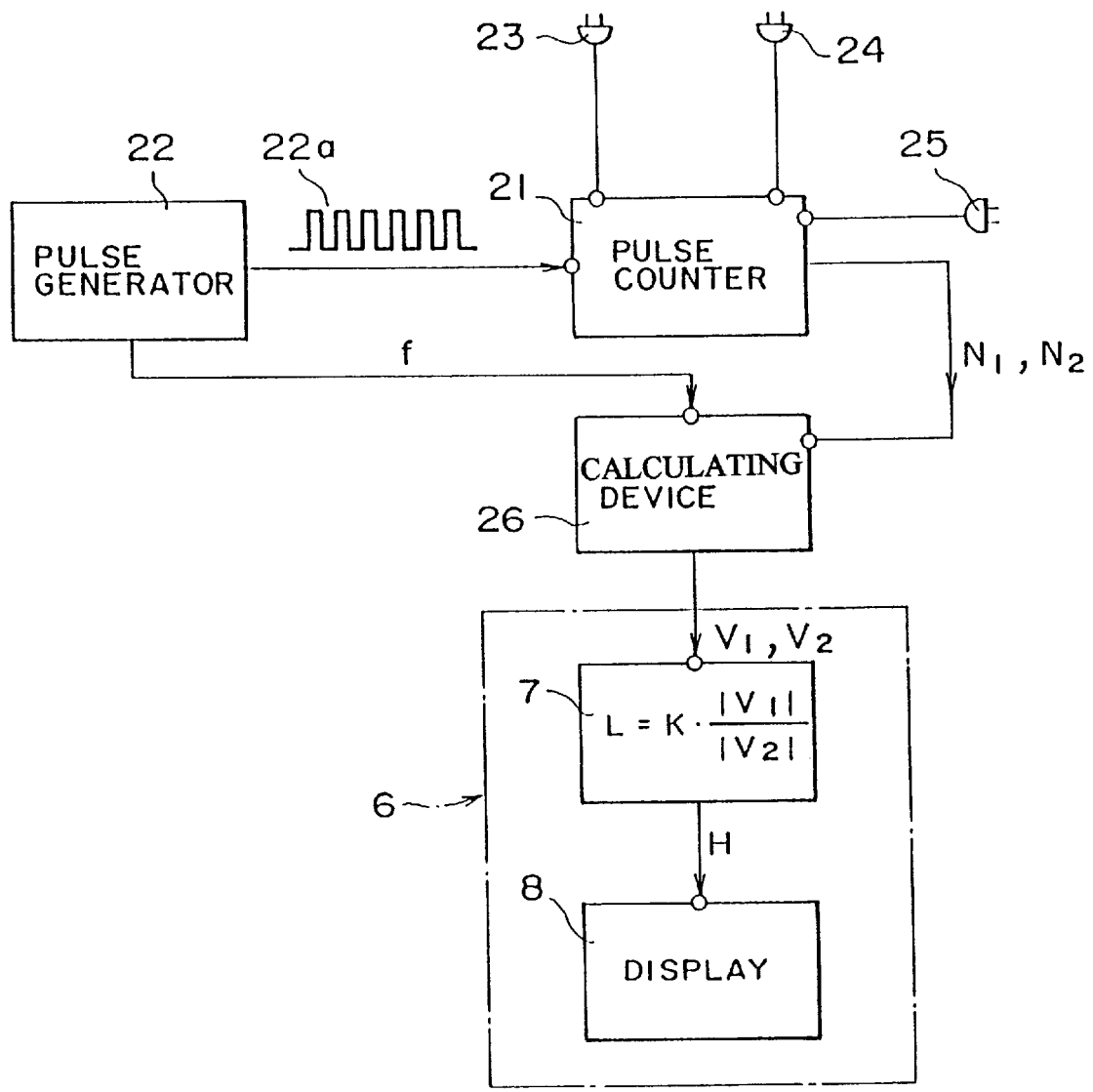
FIG. 2 is a circuit diagram of a velocity detector circuit of the indenter hammer.
Figure 3:
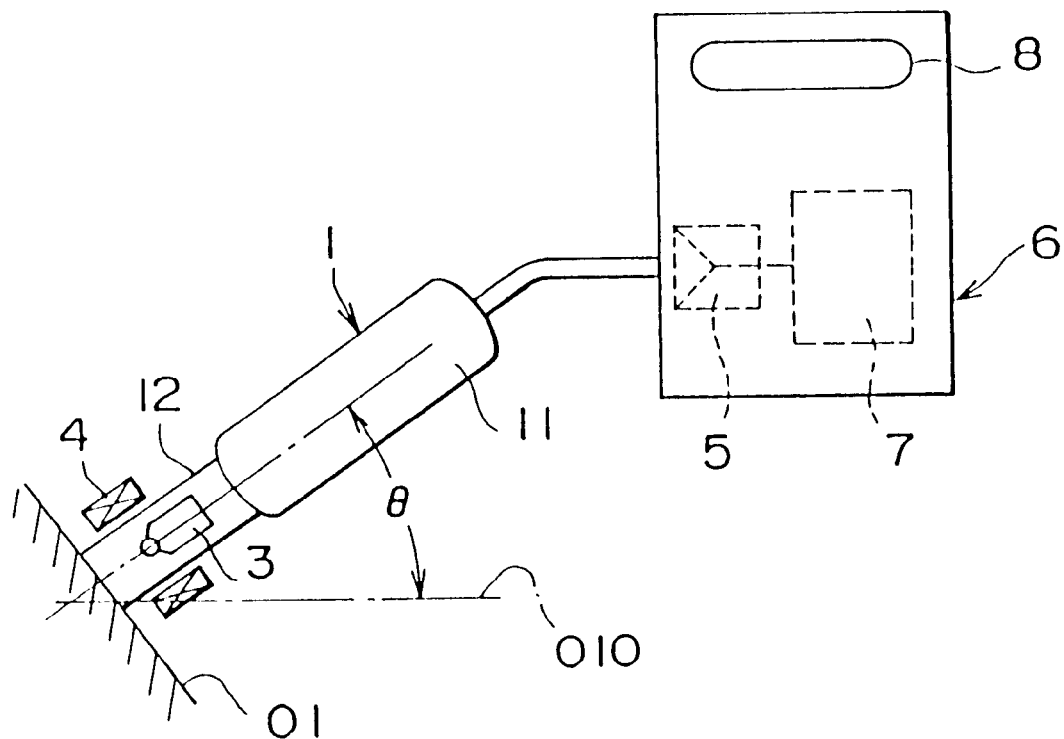
FIG. 3 is a diagram schematically showing a conventional Equotip type hardness tester.
Figure 4:
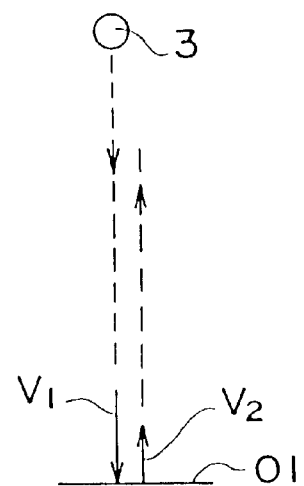
FIG. 4 is a diagram schematically showing the measuring principle in the Equotip type hardness tester.
Figure 5:
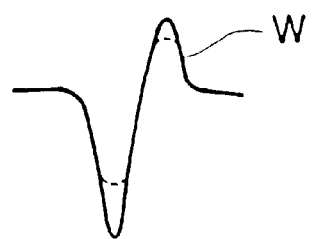
FIG. 5 is a pulse waveform in a conventional velocity detector portion.

A method of detecting velocities of the indenter hammer in an Equotip type hardness tester as an embodiment of the invention and an Equotip type hardness tester in which the aforesaid detecting method is carried out will be described with reference to the accompanying drawings. FIG. 1 is a schematic diagram showing the sensor portion for measuring the velocities of the indenter hammer and FIG. 2 is a circuit diagram of the detector circuit of the indenter hammer velocities. Reference numerals in FIG. 1 and FIG. 2 like those in FIG. 3 and FIG. 4 denote virtually the same members.

In the embodiment of the described type, the hardness tester comprises a tubular member of measuring cylinder 12 having an axial passage 12a, and an indenter hammer 2 mounted within the axial passage 12 of the measuring cylinder 12 for undergoing axial movement therein in a forward direction to impact a specimen 01 and in a rearward direction away from the specimen immediately after the impaction. A set of light projecting holes 1a and 2a constituting the sensor for measuring the velocities of the indenter hammer 3 (impacting velocity against and rebounding velocity from the specimen 01) are provided in the vicinity of the front end portion of the measuring cylinder 12 a distance S apart in the axial direction of the measuring cylinder 12 as shown in FIG. 1.

Further, in the positions of the measuring cylinder 12 opposing the light projecting holes 1a and 2a, there are provided a set of light receiving holes 1b and 2b the same distance S apart.

The light projecting holes 1a and 2a are provided with light sources 13 and 14 formed of a lens and a lamp and the light receiving holes 1b and 2b are provided with photodetector devices 23 and 24 of a photodiode or the like. As the light source, other than the lamp, that employing a semiconductor, such as a light-emitting diode or a laser beam, may be used. The light projecting hole 1a, the light receiving hole 1b and the corresponding light source 13 and the photodetector device 23 constitute a first detecting device for detecting the indenter hammer 3 during movement thereof within the axial passage of the measuring cylinder 12 in the forward and rearward directions. The light projecting hole 2a, the light receiving hole 2b and the corresponding light source 14 and the photodetector device 24 constitute a second detecting device for detecting the indenter hammer 3 during movement thereof within the axial passage of the measuring cylinder 12 in the forward and rearward directions.

Further, at the portions close to the forefront of the measuring cylinder 12, there are provided a light projecting hole 3a and a light receiving hole 3b opposing each other and a light source 15 is provided for the light projecting hole 3a, while a photodetector device 25 is provided for the light receiving hole 3b.

In the above described structure, at the time of measurement, the indenter hammer 3 advances in the direction of the arrow A and, when it reaches the position of the light projecting hole 1a, the light beam being emitted from the light source 13 and receiving by the photodetector device 23 through the light projecting hole 1a and the light receiving hole 1b is blocked by the indenter hammer 3.

When the indenter hammer 3 further advances in the direction of the arrow A and reaches the position of the light projecting hole 2a, the light beam being emitted from the light source 14 and received by the photodetector device 24 through the light projecting hole 2a and the light receiving hole 2b is blocked by the indenter hammer 3.

The indenter hammer 3 further advances in the direction of the arrow A, impacts against and rebounds from the specimen 01, and moves in the direction opposite to the arrow A. Then, first, the light beam being received by the photodetector device 24 is blocked and, then, the light beam being received by the photodetector device 23 is blocked.

The time $T_1$ elapsed the blocking of the light to the photodetector device 23 and the blocking of the light to the photodetector device 24 and the time $T_2$ elapsed between the blocking of the light to the photodetector device 24 and the blocking of the light to the photodetector device 23 can be measured by a later described electronic circuit (of FIG. 2) in accordance with ON-OFF signals from the photodetector devices 23 and 24.

Meanwhile, the distance between the light projecting hole 1a and the light projecting hole 2a, i.e., the distance between the light receiving hole 1b and the light receiving hole 2b, is known (to be S in the present embodiment). Hence, the impacting velocity $V_1$ of the indenter hammer 3 can be obtained by calculating the ratio of S to $T_1$ ($S/T_1$), while the rebounding velocity $V_2$ of the indenter hammer 3 can be obtained by calculating the ratio of S to $T_2$ ($S/T_2$).

Now, the circuit for calculating the times $T_1$ and $T_2$ in accordance with the ON-OFF signals from the photodetector devices 23 and 24 will be described.

Referring to FIG. 2, reference numeral 21 denotes a pulse counter for counting timing pulses 22a (clock pulses) generated in a pulse generator 22.

The pulse counter 21 is adapted such that signals from the photodetector devices 23, 24, and 25 are input thereto. In the pulse counter 21, the number $N_1$ of the timing pulses 22a from the moment the signal indicating that the light to the photodetector device 23 was blocked (an OFF signal from the photodetector device 23) was input to the moment the signal indicating that the light to the photodetector device 24 was blocked (an OFF signal from the photodetector device 24) and the number $N_2$ of the timing pulses 22a from the moment an OFF signal from the photodetector device 24 was input to the moment an OFF signal from the photodetector device 23 was input are respectively counted.

$T_1$ and $T_2$ are calculated in a calculating device 26 in accordance with the numbers of pulses $N_1$ and $N_2$ counted by the pulse counter 21 and the frequency f of the timing pulse 22a and, further, the impacting velocity $V_1$ and the rebounding velocity $V_2$ of the indenter hammer 3 are calculated in accordance with $T_1$, $T_2$, and the distance S between the light receiving holes 1b and 2b.

The light projecting hold 3a and the light receiving hole 3b, as well as the light source 15 and the photodetector device 25, are provided for confirming that the indenter hammer 3 has impacted the specimen (face) and rebounded therefrom. Namely, when ON-OFF signals from each of the photodetector devices have been received by the pulse counter 21 in the order of an OFF signal from the photodetector device 23→an OFF signal from the photodetector device 24→an OFF signal from the photodetector device 25→an ON signal from the same, it is determined that the indenter hammer 3 properly rebounded and, thereupon, the number of pulses $N_1$ and $N_2$ are output from the pulse counter 21. A processing device 7, such as a central processing unit (CPU), associated with a display unit 6 receives information from the calculating device 26 on the velocities $V_1$ and $V_2$ and calculates the hardness L of the specimen 01. The calculated hardness L of the specimen 01 is then displayed on a display 8.

Thus, in the embodiment, since the indenter hammer velocity (detecting) sensor is of a photoelectric type, it is possible to carry out the detection having the detecting accuracy of the velocity of the indenter hammer unaffected by the indenter hammer velocity and, further, the measurement can be carried out without being affected by environmental magnetism or magnetism in the specimen.

According to the Equotip type hardness tester of the invention and the method of detecting velocities of the indenter hammer of the hardness tester, as described above in detail, the following effects or advantages can be obtained:

(1) The time required for the indenter hammer to travel the distance between the light receiving holes during its impacting course and the time required for the same to travel the distance between the light receiving holes during its rebounding course are respectively measured and, in accordance with each of the measured times and the distance between the light receiving holes, the impacting velocity and rebounding velocity of the indenter hammer against and from the specimen (face) can be calculated.

(2) The aforesaid times can be calculated by using a pulse counter and by having numbers of timing pulses counted by the pulse counter.

(3) Since the indenter hammer velocity (detecting) sensor is provided by that of a photoelectric type, it is made possible to carry out the detection having the detecting accuracy of the velocity of the indenter hammer unaffected by the indenter hammer velocity.

(4) The measurements can be carried out unaffected by environmental magnetism or a magnetized specimen.

What is claimed is:

1. A rebound-type hardness tester comprising:
   a measuring cylinder comprised of a body having an axial passage;
   a first light projecting hole formed in the body of the measuring cylinder;
   a first light receiving hole formed in the body of the measuring cylinder;
   a first light source for projecting light through the first light projecting and first light receiving holes;
   a first photodetector device for receiving light projected from the first light source and passing through the first light projecting and first light receiving holes;
   a second light projecting hole formed in the body of the measuring cylinder at a preselected distance from the first light projecting hole;
   a second light receiving hole formed in the body of the measuring cylinder;
   a second light source for projecting light through the second light projecting and second light receiving holes;
   a second photodetector device for receiving light projected from the second light source and passing through the second light projecting and second light receiving holes;
   an indenter hammer mounted within the passage of the measuring cylinder body for undergoing axial movement therein in a forward direction to impact a specimen and in a rearward direction away from the specimen immediately after the impaction, and for temporarily blocking the light emitted from the first and second light sources and received by the first and second photodetector devices, respectively, during respective movement in the forward and rearward directions;

a spring member for generating a spring force to accelerate the indenter hammer in the forward direction to impact the specimen:

measuring means for measuring a first time value corresponding to a time elapsed between the blocking of the light to the first photodetector device and the blocking of the light to the second photodetector device by the indenter hammer during movement thereof in the forward direction, and for measuring a second time value corresponding to the time elapsed between the blocking of the light to the second photodetector device and the blocking of the light to the first photodetector device by the indenter hammer during movement thereof in the rearward direction;

calculating means for calculating an impacting velocity of the indenter hammer corresponding to a velocity of the indenter hammer immediately before the impact thereof with the specimen in accordance with the first time value measured by the measuring means and the preselected distance between the first and second light projecting holes, and for calculating a rebounding velocity of the indenter hammer corresponding to a velocity of the indenter hammer immediately after the impact thereof with the specimen in accordance with the second time value measured by the measuring means and the preselected distance between the first and second light projecting holes; and processing means for calculating a hardness of the specimen in accordance with the impacting velocity and the rebounding velocity calculated by the calculating means.

2. A rebound-type hardness tester according to claim 1; further comprising a display for displaying the hardness calculated by the processing means.

3. A rebound-type hardness tester according to claim 1; wherein the spring member comprises a coil spring.

4. A rebound-type hardness tester according to claim 1; wherein the measuring means comprises a pulse generator for generating timing pulses during blocking of the light to the first and second photodetector devices by the indenter hammer; a pulse counter for counting a first number of timing pulses from the blocking of the light to the first photodetector device until the blocking of the light to the second photodetector device by the indenter hammer during movement thereof in the forward direction, and for counting a second number of timing pulses from the blocking of the light to the second photodetector device until the blocking of the light to the first photodetector device by the indenter hammer during movement thereof in the rearward direction; and a calculating device for calculating the first time value and the second time value in accordance with the first and second timing pulses, respectively, counted by the pulse counter.

5. A rebound-type hardness tester according to claim 1; further comprising confirmation means for confirming that the indenter hammer has impacted the specimen and rebounded therefrom.

6. A rebound-type hardness tester according to claim 5; wherein the confirmation means comprises a third light projecting hole formed in the body of the measuring cylinder and having a third light source for projecting light, and a third light receiving hole formed in the body of the measuring cylinder and having a third photodetector device for receiving light projected from the third light source.

7. A rebound-type hardness tester comprising:

a tubular member having an axial passage;

an indenter hammer mounted within the axial passage of the tubular member for undergoing axial movement therein in a forward direction to impact a specimen and in a rearward direction away from the specimen immediately after the impaction;

a biasing member for generating a biasing force to accelerate the indenter hammer in the forward direction to impact the specimen;

a first detecting device for detecting passage of the indenter hammer during movement thereof in the forward and rearward directions;

a second detecting device disposed at a preselected distance from the first detecting device for detecting passage of the indenter hammer after detection thereof by the first detection device during movement of the indenter hammer in the forward direction, and for detecting passage of the indenter hammer before detection thereof by the first detection device during movement of the indenter hammer in the rearward direction;

a measuring device for measuring a first time value corresponding to a time elapsed between the detection of the indenter hammer by the first detection device and the detection of the indenter hammer by the second detection device during movement of the indenter hammer in the forward direction, and for measuring a second time value corresponding to the time elapsed between the detection of the indenter hammer by the second detection device and the detection of the indenter hammer by the first detection device during movement of the indenter hammer in the rearward direction;

a calculating device for calculating an impacting velocity of the indenter hammer corresponding to a velocity of the indenter hammer immediately before the impact thereof with the specimen in accordance with the first time value measured by the measuring device and the preselected distance between the first and second detecting devices, and for calculating a rebounding velocity of the indenter hammer corresponding to a velocity of the indenter hammer immediately after the impact thereof with the specimen in accordance with the second time value measured by the measuring device and the preselected distance between the first and the second detecting devices; and a processing device for calculating a hardness of the specimen in accordance with the impacting velocity and the rebounding velocity calculated by the calculating device.

8. A rebound-type hardness tester according to claim 7; wherein the first detecting device comprises a first light projecting hole formed in the body of the measuring cylinder, a first light receiving hole formed in the body of the measuring cylinder, a first light source for projecting light through the first light projecting and first light receiving holes, and a first photodetector device for receiving light projected from the first light source and passing through the first light projecting and first light receiving holes; and wherein the second detecting device comprises a second light projecting hole formed in the body of the measuring cylinder at a preselected distance from the first light projecting hole, a second light receiving hole formed in the body of the measuring cylinder, a second light source for projecting light through the second light projecting and second light receiving holes, and a second photodetector device for receiving light projected from the second light source and passing through the second light projecting and second light receiving holes.

9. A rebound-type hardness tester according to claim 8, further comprising a display for displaying the hardness calculated by the processing device.

10. A rebound-type hardness tester according to claim 8, wherein the biasing member comprises a coil spring.

11. A rebound-type hardness tester according to claim 8, wherein the measuring device comprises a pulse generator for generating timing pulses during detection of the indenter hammer by the first and second detection devices; a pulse counter for counting a first number of timing pulses beginning at the detection of the indenter hammer by the first detection device until the detection of the indenter hammer by the second detection device during movement of the indenter hammer in the forward direction, and for counting a second number of timing pulses beginning at the detection of the indenter hammer by the second detection device until the detection of the indenter hammer by the first detection device during movement of the indenter hammer in the rearward direction.

12. A rebound-type hardness tester according to claim 8, further comprising a third detecting device for detecting that the indenter hammer has impacted the specimen and rebounded therefrom.

* * * * *